(12) United States Patent
Sonobe et al.

(10) Patent No.: US 8,920,796 B2
(45) Date of Patent: *Dec. 30, 2014

(54) ADSORBENT FOR ORAL ADMINISTRATION, AND AGENT FOR TREATING OR PREVENTING RENAL OR LIVER DISEASE

(75) Inventors: Naohiro Sonobe, Iwaki (JP); Takashi Wakahoi, Fukushima (JP)

(73) Assignee: Kureha Corporation, Tokyo (JP)

(*) Notice: Subject to any disclaimer, the term of this patent is extended or adjusted under 35 U.S.C. 154(b) by 762 days.

This patent is subject to a terminal disclaimer.

(21) Appl. No.: 10/969,998

(22) Filed: Oct. 22, 2004

(65) Prior Publication Data

US 2005/0112114 A1    May 26, 2005

(30) Foreign Application Priority Data

Oct. 22, 2003 (JP) ................................. 2003-362498
Sep. 14, 2004 (JP) ................................. 2004-266198

(51) Int. Cl.
| | | |
|---|---|---|
| A01N 59/00 | (2006.01) | |
| A01N 25/00 | (2006.01) | |
| A61K 33/44 | (2006.01) | |
| A61K 9/14 | (2006.01) | |
| A61K 33/00 | (2006.01) | |
| A61K 47/00 | (2006.01) | |
| B01J 20/00 | (2006.01) | |
| C01B 31/08 | (2006.01) | |

(52) U.S. Cl.
CPC .............. A61K 33/44 (2013.01); Y10S 514/893 (2013.01)
USPC ........... 424/125; 424/600; 424/489; 502/418; 502/400; 502/416; 514/769; 514/893

(58) Field of Classification Search
CPC .............................. A61K 33/44; A61K 9/143
USPC .......... 424/125, 600, 489; 502/418, 400, 416; 514/769, 893
See application file for complete search history.

(56) References Cited

U.S. PATENT DOCUMENTS

| | | | |
|---|---|---|---|
| 4,681,764 A | 7/1987 | Endo et al. | |
| 5,554,370 A | 9/1996 | Uehara et al. | |
| 5,556,622 A | 9/1996 | Uehara et al. | |
| 5,573,761 A * | 11/1996 | Ise et al. ......... | 424/125 |
| 6,372,289 B1 * | 4/2002 | Hickman ............ | 427/228 |
| 7,651,974 B2 * | 1/2010 | Sonobe et al. ..... | 502/418 |
| 8,309,130 B2 * | 11/2012 | Sonobe et al. ..... | 424/484 |
| 2004/0141963 A1 | 7/2004 | Umekawa et al. | |

FOREIGN PATENT DOCUMENTS

| | | |
|---|---|---|
| CN | 1114194 A | 1/1996 |
| EP | 0 029 715 A1 | 6/1981 |
| EP | 0 595 715 A1 | 5/1994 |
| EP | 0 595 716 A1 | 5/1994 |
| EP | 0 620 006 A2 | 10/1994 |
| EP | 0 688 566 A1 | 12/1995 |
| EP | 0 688 567 A1 | 12/1995 |
| EP | 0 711 561 A2 | 5/1996 |
| EP | 1 249 241 A1 | 10/2002 |
| EP | 1 440 692 A1 | 7/2004 |
| EP | 1 500 397 A1 | 1/2005 |
| GB | 2 012 257 A | 7/1979 |
| GB | 2 028 385 A | 1/1980 |
| GB | 2025385 A * | 1/1980 |
| GB | 2 053 176 A | 2/1981 |
| GB | 2280898 A | 2/1995 |
| JP | 51126390 A | 11/1976 |
| JP | 54089010 A | 7/1979 |
| JP | 5628766 | 8/1979 |
| JP | 56005313 A | 1/1981 |
| JP | 08-128766 A | 3/1981 |
| JP | 56-28766 | 3/1981 |
| JP | 56-73541 A | 6/1981 |
| JP | 56073542 A | 6/1981 |
| JP | 82-136455 A | 8/1982 |
| JP | 57136455 | 8/1982 |
| JP | 58013613 A | 1/1983 |
| JP | 58-213613 A | 12/1983 |
| JP | 59006208 A | 1/1984 |
| JP | 61001366 B | 1/1986 |
| JP | 62-011611 A | 1/1987 |
| JP | 62011611 B | 3/1987 |
| JP | 63051161 B | 10/1988 |
| JP | 1056141 A | 3/1989 |
| JP | 1101314 A | 4/1989 |
| JP | 4338107 A | 11/1992 |

(Continued)

OTHER PUBLICATIONS

O. Otsubo et al., Direct Hemoperfusion With Noncoated Charcoal of High Adsorption Capacity Derived From Thermosetting Resin, Trans. Am. Soc. Artif. Intern. Organs, vol. XXVI, 1980, 26, pp. 124-128.

Yang et al, Preparation and Properties of Phenolic Resin-Based Activated Carbon Spheres With Controlled Pore Size Distribution, Carbon, May 2002, pp. 911-916, vol. 40—No. 6.

J. J. Grantham, Polycystic Kidney Disease, Jun. 2007, National Kidney and Urologic Diseases Information Clearinghouse, National Institute of Diabetes and Digestive and Kidney Diseases, National Institute of Health, NIH Publication No. 07-4008, pp. 1-7.

N. Reau, Hemochromatosis, Digestive Disease Library, The Johns Hopkins Medical Institutions Gastroenterology and Hepatology Resource Center, pp. 1-12.

(Continued)

Primary Examiner — Abigail Fisher
(74) Attorney, Agent, or Firm — Sughrue Mion, PLLC

(57) ABSTRACT

An adsorbent for an oral administration, comprising a surface-modified spherical activated carbon wherein an average diameter is 0.01 to 1 mm, a specific surface area determined by a BET method is 700 m²/g or more, a volume of pores having a pore diameter of 7.5 to 15000 nm is from 0.25 mL/g to 1.0 mL/g, a total amount of acidic groups is 0.30 to 1.20 meq/g, and a total amount of basic groups is 0.20 to 0.7 meq/g, is disclosed.

11 Claims, 1 Drawing Sheet

(56) References Cited

FOREIGN PATENT DOCUMENTS

| | | |
|---|---|---|
| JP | 7165407 A | 6/1995 |
| JP | 8040918 A | 2/1996 |
| JP | 8208491 A | 8/1996 |
| JP | 10316578 A | 12/1998 |
| JP | 11029485 A | 2/1999 |
| JP | 11049503 | 2/1999 |
| JP | 11060664 A | 3/1999 |
| JP | 11116648 A | 4/1999 |
| JP | 11217278 A | 8/1999 |
| JP | 11-292770 | 10/1999 |
| JP | 11-292770 A | 10/1999 |
| JP | 11-292771 A | 10/1999 |
| JP | 2000233916 A | 8/2000 |
| JP | 2001114852 A | 4/2001 |
| JP | 2001288238 A | 10/2001 |
| JP | 2002308785 A | 10/2002 |
| JP | 2004244414 A | 9/2004 |
| JP | 3672200 B2 | 7/2005 |
| JP | 3835698 B2 | 10/2006 |
| RU | 1836138 A3 | 8/1993 |
| WO | 2004039380 A1 | 5/2004 |

OTHER PUBLICATIONS

Sing et al.; "Reporting Physisorption Data for Gas/Solid Systems with Special Reference to the Determination of Surface Area and Porosity"; Pure & Applied Chemistry; vol. 57, No. 4; pp. 603-619; c. 1985; Great Britain.

H. Kitagawa, et al., "Steam Activation of Phenol-formaldehye Resin", Journal of Industrial Chemistry, vol. 73, No. 10, pp. 38-42, 1970 (abstract only).

A. Gardziella et al., "Carbon from Phenolic Resins: Carbon Yield and Volatile Components—Recent Studies", International Conference on Carbon, Essen, Germany, vol. 41, No. 7/8, pp. 461-467, Jun. 22-26, 1992.

Hiroshi Kitagawa, "Preparation of Active Carbon from Phenol-Formaldehyde Resin", a Japanese Journal "Nihon-Kagaku-Raishi" (A Chemical Society of Japan), No. 6, pp. 1144-1150, 1972.

Yutaka. Fukumoto, et al., "Production of Activated Carbon from Waste Phenol Resin", a Japanese Journal "TANSO" (Carbon), No. 188, pp. 138-142, 1999.

Shigeaki Kasoka, et al., "Preparation of Activated Fibrous Carbon from Phenolic Fabric and Its Molecular Sieving Properties", a Japanese Journal "Nihon-Kagaku-Kaishi" (A Chemial Society of Japan), No. 6, pp. 990-1000, 1987.

Katsuya Fukuyama, et al., Small angle X-ray Scattering from Glass-like Carbon and its Graphitization Behavior, a Japanese Journal "TANSO" (Carbon), No. 182, pp. 85-90, 1998.

M. Shioya, et al., "Characterization of the Structure of Carbon Fibers by Wide-Angle and Small-Angle X-ray Scatterings", a Japanese Journal "TANSO" (Carbon), No. 139, pp. 189-198, 1989.

Keiko Nishikawa, "Study on Pore Structure of Porous Carbons by Small-Angle X-ray Scattering," a Japanese Journal "TANSO" (Carbon), No. 191, pp. 71-76, 2000.

O. Otsubo, et al., "Direct hemoperfusion with non-coated charcoal of high adsorption capacity derived from thermosetting resin", Trans Am Soc Artif Intern Organs, vol. 26, pp. 124-128, 1980

Hiroshi Kitagawa, at al., "Steam Activation of Phenol-formaldehyde Resin", a Japanese Journal "Kogyo-Kagaku-Zasshi" (Journal of Industrial Chemistry), vol. 73, No. 10, pp. 2100-2104, 1970.

Shigeaki Kasaoka, et al., "Preparation of Activated Fibrous Carbon from Phenolic Fabric and Its Molecular Sieving Properties", a Japanese Journal "Nihon-Kagaku-Kaishi" (A Chemical Society of Japan), No. 6, pp. 990-1000, 1987.

Eiichi Asada, et al., a Japanese Text Book "X-sen Bunseki: Kiso-Bunseki-Kagaku Koza, No. 24" (X-ray Analysis: Basic Course of Analytical Chemistry), published by Kyoritsu Shuppan Co., Ltd., pp. 52-53, 1968.

A Japanese Text Book "Saishin-no-Tanso-Zairyo Jikken Gijutsu: Bunseki, Kaiseki-Hen" (Latest Experimental Technique of Carbon Substance), edited by Carbon Society of Japan, pp. 156-161, 2001.

"Activated carbon", a Japanese Dictionary "Kagaku-jiten" (Chemical dictionary), Oct. 2, 2000, Tokyo Kagaku Dozin Co., Ltd.

Experiment Report, "Influences of measuring and analyzing conditions on R values", Jul. 13, 2007, by Japan EnviroChemicals Co., Ltd.

"Hyperuricemia",at al., a Japanese Dictionary "Nanzando's Medical Dictionary", Mar. 25, 1991, Nanzando Co., Ltd.

"Colloid Science IV, Experimental Methodology of Colloid Science", edited by Nihon-Kagaku-Gakkai (The Chemical Society of Japan), Apr. 1, 1996, Tokyo Kagaku Dozin Co., Ltd.

Undated brochure describing the commercial product "Maririn", Gun Ei Chemical Industry Co., Ltd.

No-address Cover letter form for sending a brochure describing the commercial product "Maririn", etc., dated May 8, 2002, Gun Ei Chemical Industry Co., Ltd.

Hideki Tatsumoto, et al., "Activated carbon for recovering solvents", a Japanese Text Book "Kassei-Tanso no Oyo-Gijutsu" (Applied Technology of Activated Carbon), p. 2, 2000.

* cited by examiner

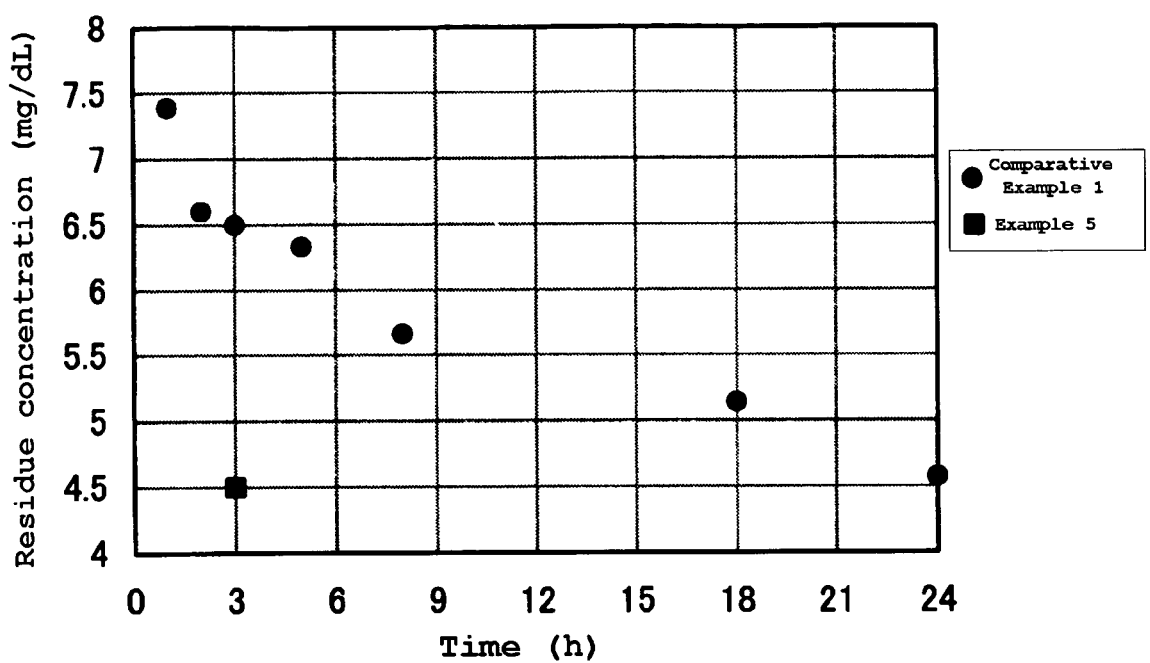

ADSORBENT FOR ORAL ADMINISTRATION, AND AGENT FOR TREATING OR PREVENTING RENAL OR LIVER DISEASE

BACKGROUND OF THE INVENTION

1. Field of the Invention

The present invention relates to an adsorbent for oral administration comprising a surface-modified spherical activated carbon having a specific pore structure. Further, the present invention relates to an agent for treating or preventing a renal or liver disease, comprising the adsorbent for oral administration as an effective component.

The adsorbent for oral administration, according to the present invention, exhibits a high adsorbability of harmful toxins in a body, and therefore, can adsorb many toxins within a given period of time wherein toxins must be adsorbed, during a retention period from the oral administration to an excretion.

2. Description of the Related Art

In patients suffering a lack of a renal function or a liver function, harmful toxic substances are accumulated or formed in bodies, such as blood, with a progress of a disorder of the organ functions, and thus an encephalopathia occurs, such as a disturbance of consciousness or uremia. Yearly, there is a growing number of such patients, and therefore, the development of an organ-substitute apparatus or medicament having a function to remove toxic substances from bodies, in place of such defective organs, has become a serious problem. A method for removing toxic substances by hemodialysis as an artificial kidney is prevalent. Nevertheless, the hemodialysis-based artificial kidney requires a special apparatus, and thus, a skilled specialist is required from a safe operation standpoint. Further, blood must be taken from a patient's body, and thus, there are disadvantages in that patients must bear high physical, mental and economic burdens. Accordingly, hemodialysis is not satisfactory.

As a means of remedying the above disadvantages, an oral adsorbent which can be orally administered and cure a disorder of renal and liver functions was developed and utilized [Japanese Examined Patent Publication (Kokoku) No. 62-11611]. The adsorbent disclosed in Japanese Examined Patent Publication (Kokoku) No. 62-11611 comprises a porous spherical carbonaceous substance having particular functional groups, that is, a surface-modified spherical activated carbon, having a high safety factor and stable to a body, and having a useful selective adsorbability; that is, an excellent adsorbability of harmful substances in the presence of a bile acid in an intestine, and a low adsorbability of useful substances such as digestive enzymes in the intestine. For these reasons, the oral adsorbent is widely and clinically used for a patient suffering from a disorder of a liver or renal function, as an adsorbent having few side effects such as constipation. The above adsorbent disclosed in Japanese Examined Patent Publication (Kokoku) No. 62-11611 was prepared by forming a spherical activated carbon from a pitch such as a petroleum pitch as a carbon source, and then carrying out an oxidizing treatment and a reducing treatment.

Further, Japanese Patent No. 3522708 [Japanese Unexamined Patent Publication (Kokai) No. 2002-308785] discloses an adsorbent for oral administration providing an improvement in the above useful selective adsorbability; that is, an excellent adsorbability of harmful substances and a low adsorbability of useful substances in the intestine. The adsorbent for oral administration disclosed in Japanese Patent No. 3522708 is based on a finding that the above selective adsorbability is improved within a special scope of a pore volume, that is, when a volume of pores having a pore diameter of 20 to 15000 nm is from not less than 0.04 mL/g to less than 0.10 mL/g. The adsorbent for oral administration is very effective in the treating of wherein diseases that a sufficient adsorption of toxins and a reduced adsorption of useful substances in the intestine are desired.

SUMMARY OF THE INVENTION

The above selective adsorbability is a very important property of the oral adsorbent composed of the surface-modified spherical activated carbon. On the other hand, it is also very important to adsorb and remove as many as possible of toxins in a body, and as soon as possible. In general, the oral adsorbent composed of the surface-modified spherical activated carbon has a retention period of about 3 to 5 hours in an upper portion of a small intestine. Therefore, a surface-modified spherical activated carbon having a high adsorbability for a period of about 3 hours after contacting toxins, and an excellent initial adsorbability, is desirable.

As shown in Examples below, however, the oral adsorbents disclosed in Japanese Examined Patent Publication (Kokoku) No. 62-11611 and Japanese Patent No. 3522708 do not have a high adsorbability for about 3 hours after contacting toxins, and are conveyed to a lower portion of a small intestine and a large intestine, and then excreted outside of a body, while the adsorbability is not completely exhausted, but enough adsorbability is still maintained.

Therefore, the inventors of the present invention engaged in intensive research to develop an oral adsorbent having a high adsorbability, that is, an oral adsorbent capable of adsorbing and removing a large amount of toxins, and having an excellent initial adsorption rate, and found that an oral adsorbent having an excellent adsorbability and an excellent initial adsorption rate can be obtained in a pore volume scope different from that of the conventionally known oral adsorbents. Further, the inventors of the present invention surprisingly found that the above adsorption rate does not always correlate with an increase or decrease of a specific surface area. For example, if the specific surface area is decreased, increases of the adsorbability and the initial adsorption rate were observed. The oral adsorbent found by the inventors can adsorb a large amount of toxins for 3 hours during the retention period in the upper portion of a small intestine, and thus, makes it possible to reduce a dosage.

The present invention is based on the above findings.

Accordingly, the object of the present invention is to provide an oral adsorbent exhibiting a high adsorbability of a large amount of toxins and an excellent initial adsorption rate.

Other objects and advantages of the present invention will be apparent from the following description.

In accordance with the present invention, there is provided an adsorbent for an oral administration, comprising a surface-modified spherical activated carbon wherein an average diameter is 0.01 to 1 mm, a specific surface area determined by a BET method is 700 m²/g or more, a volume of pores having a pore diameter of 7.5 to 15000 nm is from 0.25 mL/g to 1.0 mL/g, a total amount of acidic groups is 0.30 to 1.20 meq/g, and a total amount of basic groups is 0.20 to 0.7 meq/g.

In accordance with another aspect of the present invention, there is provided a pharmaceutical composition comprising the surface-modified spherical activated carbon as above.

In accordance with still another aspect of the present invention, there is provided a method for treating or preventing a renal or liver disease, comprising administering to a subject in need thereof, the surface-modified spherical activated carbon as above at an effective amount therefor.

In accordance with still another aspect of the present invention, there is provided a use of the surface-modified spherical activated carbon as above, for preparing the pharmaceutical composition for treating or preventing a renal or liver disease.

The adsorbent for an oral administration of the present invention has a high adsorbability, and thus an excellent initial adsorbability. Therefore, the oral adsorbent of the present invention can very rapidly adsorb harmful toxins in a body during the general retention period in an upper portion of a small intestine, and is efficient as an agent for treating or preventing a renal or liver disease. Further, a dosage can be reduced in comparison with a conventional oral adsorbent.

BRIEF DESCRIPTION OF DRAWINGS

FIG. 1 is a graph showing the results of a comparison of adsorption rates of DL-β-aminoisobutyric acid.

DESCRIPTION OF THE PREFERRED EMBODIMENTS

The surface-modified spherical activated carbon used as the adsorbent for an oral administration of the present invention has a volume of pores having a pore diameter of 7.5 to 15000 nm of from 0.25 mL/g to 1.0 mL/g, as above.

On the contrary, in Examples 1 to 3 of the above-mentioned Japanese Examined Patent Publication (Kokoku) No. 62-11611, adsorbents wherein a pore volume having a pore radius of 37.5 to 75000 angstrom is 0.20 to 0.23 mL/g were actually prepared, and an excellent adsorbability of β-aminoisobutyric acid, γ-amino-n-butyric acid, dimethylamine, and octopamine was actually confirmed. In this connection, Japanese Examined Patent Publication (Kokoku) No. 62-11611 generally discloses an adsorbent comprising a porous spherical carbonaceous substance wherein a pore volume having a pore radius of 100 to 75000 angstrom, that is, a volume of pores having a diameter of 20 to 15000 nm, is 0.1 to 1 mL/g. However, only the adsorbents wherein a pore volume having a pore radius of 37.5 to 75000 angstrom is 0.20 to 0.23 mL/g are concretely disclosed in Examples 1 to 3 thereof. Further, Japanese Examined Patent Publication (Kokoku) No. 62-11611 does not disclose that an adsorption amount is increased and an initial adsorption rate is improved when a volume of pores having a pore diameter of 7.5 to 15000 nm is from 0.25 mL/g to 1.0 mL/g. The structure of the porous spherical carbonaceous substance of the present invention wherein a volume of pores having a pore diameter of 7.5 to 15000 nm is from 0.25 mL/g to 1.0 mL/g is different in the pore volume of that of the porous spherical carbonaceous substance disclosed in Japanese Examined Patent Publication (Kokoku) No. 62-11611 wherein a pore volume having a pore radius of 37.5 to 75000 angstrom, that is, a volume of pores having a diameter of 7.5 to 15000 nm, is 0.20 to 0.23 mL/g.

The pores, that is, the pores having a diameter of 7.5 to 15000 nm, in the porous spherical carbonaceous substance disclosed in Japanese Examined Patent Publication (Kokoku) No. 62-11611 were formed mainly by a dissolution and extraction of naphthalene. In this case, crystalline shapes can be controlled by an amount of naphthalene added to a pitch and an extracting rate, and thus, the structure of the pores can be controlled by the extraction thereof. In order to increase the pore volume by means of the technique known at the time when Japanese Examined Patent Publication (Kokoku) No. 62-11611 was filed, it is necessary to increase an amount of naphthalene extracted. For this, it is supposed that an amount of naphthalene added should be increased. In fact, when the amount of naphthalene added is excessively increased, the extracting conditions of naphthalene change, and a number of big pores are easily formed to cause a problem in that the strength of the porous spherical pitch of porous spherical activated carbon is lowered. Further, an amount of naphthalene deposited on a surface of a spherical pitch product is increased, and thus, a surface shape of the spherical pitch is deteriorated. Therefore, an amount of naphthalene which may be added was limited in the conventional technique at the time when Japanese Examined Patent Publication (Kokoku) No. 62-11611 was filed.

According to a subsequent technological advancement in the control of a pore structure, an amount of naphthalene added is now able to be increased in comparison with the conventional method. Further, for example, the pore structure could be controlled independently of an amount of naphthalene added. Therefore, the surface-modified spherical activated carbon of the present invention wherein a volume of pores having a pore diameter of 7.5 to 15000 nm is from 0.25 mL/g to 1.0 mL/g can be prepared.

Japanese Patent No. 3522708 discloses that an adsorbent wherein a volume of pores having a pore diameter of 20 to 15000 nm is from not less than 0.04 mL/g to less than 0.10 mL/g exhibits an excellent selective adsorbability. It also discloses in Examples concrete data showing the selective adsorbability, that is, a low adsorbability of useful α-amylase, while a high adsorbability of a toxic β-aminoisobutyric acid is maintained. However, it does not disclose the surface-modified spherical activated carbon as used in the present invention wherein a volume of pores having a pore diameter of 7.5 to 15000 nm is from 0.25 mL/g to 1.0 mL/g. Further, it does not disclose that an adsorbability is increased and an initial adsorption rate is improved when a volume of pores having a pore diameter of 7.5 to 15000 nm is from 0.25 mL/g to 1.0 mL/g.

It was believed that an adsorbability of an oral adsorbent is dependent on the number and/or the volume of the pores which act as an adsorbing site, and thus the adsorbability of the oral adsorbent can be improved by increasing a specific surface area of the oral adsorbent. As shown in Examples below, however, an adsorbability of an oral adsorbent, that is, an amount of harmful substances adsorbed by an oral adsorbent, is increased in a range of a pore volume of 0.25 mL/g or more, and does not correlate to an increase of a specific surface area.

A carbon source for the surface-modified spherical activated carbon used as the adsorbent for oral administration of the present invention may be any carbon-containing material. The carbon-containing material which may be used is, for example, a synthetic resin or pitch. The synthetic resin may be a heat-fusible resin or a heat-infusible resin. The term "heat-fusible resin" as used herein means a resin from which an activated carbon cannot be produced because it is melted and then partially decomposed as a temperature is raised, if an activation treatment is carried out before a treatment to impart infusibility. However, when the heat-fusible resin is treated to impart infusibility, and then is activated, an activated carbon can be produced therefrom. On the contrary, the heat-infusible resin means a resin from which an activated carbon can be produced without melting or decomposition as a temperature is raised, even if a treatment to impart infusibility is not carried out in advance. The treatment to impart infusibility is, for example, an oxidation treatment carried out at 150° C. to 400° C. under an atmosphere containing oxygen, as mentioned below.

A typical example of the heat-fusible resin is a thermoplastic resin, such as a cross-linked vinyl resin. A typical example of the heat-infusible resin is a thermosetting resin, such as a phenol or furan resin. Any known thermoplastic or thermosetting resin from which a spherical shape is formed can be used. When the surface-modified spherical activated carbon is produced from the cross-linked vinyl resin, the above treatment to impart infusibility is necessary. On the other hand, the above treatment to impart infusibility is not necessary, when the surface-modified spherical activated carbon is produced from an ion-exchange resin prepared by applying functional groups to the cross-linked vinyl resin. It is believed that the cross-linked resin is modified from the heat-fusible resin to the heat-infusible resin by the treatment used to introduce the functional groups thereto, and the functional groups introduced thereby. That is, the cross-linked vinyl resin belongs to the heat-fusible resin as used herein, whereas the ion-exchange resin belongs to the heat-infusible resin as used herein.

In the present invention, an ion-exchange resin, a cross-linked vinyl resin, or pitch is preferably used, and an ion-exchange resin or a cross-linked vinyl resin is more preferably used, as a carbon source.

When the heat-infusible resin such as an ion-exchange resin is used as a carbon source for the preparation of the surface-modified spherical activated carbon used as the adsorbent for oral administration of the present invention, a method substantially the same as a conventional method for production from pitch can be used. For example, a spherical material of a heat-infusible resin is initially activated at 700 to 1000° C. in a gas stream reactive with carbon (for example, steam or carbon dioxide gas) to obtain the spherical activated carbon. The term "activated carbon" as used herein means a porous product prepared by a heat-treatment of a carbon precursor such as a spherical heat-infusible resin, and a subsequent activation, and the term "spherical activated carbon" as used herein means an activated carbon having a spherical shape and a specific surface area of 100 $m^2/g$ or more. In the present invention, the surface-modified spherical activated carbon having a specific surface area of 700 $m^2/g$ or more is used. An average particle size of the spherical heat-infusible resin used as a starting material is preferably about 0.02 mm to 1.5 mm.

When the heat-fusible resin such as a cross-linked vinyl resin is used as a carbon source, the spherical material of a heat-fusible resin is softened by the heat-treatment and changed to an aspheric shape, or fused together by the heat-treatment. The softening can be inhibited by an oxidation at 150° C. to 400° C. in an atmosphere containing oxygen, as a treatment to impart infusibility before the activation as above.

Further, if many pyrolysis gases or the like are generated by the heat-treatment of the spherical heat-infusible resin which has been treated to impart infusibility or the spherical heat-infusible resin, pyrolysis products may be removed in advance by carrying out a pre-calcination, prior to the treatment imparting infusibility.

When pitch is used as a carbon source for the production of the surface-modified spherical activated carbon used as the adsorbent for oral administration of the present invention, the surface-modified spherical activated carbon of the present invention can be produced by activating a metal-containing spherical carbonaceous material to obtain a spherical activated carbon wherein a volume of pores having a pore diameter of 7.5 to 15000 nm is from 0.25 mL/g to 1.0 mL/g; washing with an acid to remove the metal, and oxidizing, and then reducing to modify the surface.

The spherical activated carbon wherein a volume of pores having a pore diameter of 7.5 to 15000 nm is from 0.25 mL/g to 1.0 mL/g can be prepared by, for example, the following methods.

A dicyclic or tricyclic aromatic compound having a boiling point of 200° C. or more or a mixture thereof is added as an additive to a pitch such as a petroleum pitch or a coal pitch. The whole is heated and mixed, and then shaped to obtain a shaped pitch. Then, the shaped pitch is dispersed and granulated in hot water at 70° C. to 180° C., with stirring, to obtain a microspherical shaped pitch. Further, the additive is extracted and removed from the shaped pitch by a solvent having a low solubility to the pitch but a high solubility to the additive, to thereby obtain a spherical porous pitch.

The purpose of the addition of the aromatic compound to the raw pitch is that the porous pitch is produced by extracting and removing the additive from the spherically shaped pitch, whereby a structure control and a calcination of the carbonaceous material by oxidization in the subsequent steps is made easier. As the additive, for example, naphthalene, methylnaphthalene, phenyl-naphthalene, benzyl-naphthalene, methylanthracene, phenanthrene, or biphenyl may be used alone or in a mixture thereof. An amount of the additive added to the pitch is preferably 10 to 50 parts by weight of the aromatic compound with respect to 100 parts by weight of the pitch.

It is preferable that the pitch and the additive are mixed under a melted condition with heating, to achieve a homogeneous mixing. Further, it is preferable that the mixture of the pitch and the additive is shaped to form particles having a particle size of about 1 mm or less, so that the additive can be easily extracted from the mixture. The shaping may be conducted during the melted condition, or by grinding the mixture after cooling.

A preferable solvent used to extract and remove the additive from the mixture of the pitch and the additive may be, for example, an aliphatic hydrocarbon, such as butane, pentane, hexane, or heptane, a mixture comprising an aliphatic hydrocarbon as a main component, such as naphtha or kerosene, or an aliphatic alcohol, such as methanol, ethanol, propanol, or butanol.

The additive may be removed from the shaped mixture by extracting the additive with the solvent from the shaped mixture of the pitch and the additive, while maintaining the shape. It is assumed that, upon the extraction, through-holes of the additive are formed in the shaped product, and a shaped pitch having a uniform porosity can be obtained.

Then, the resulting spherical porous pitch is treated to impart infusibility, that is, oxidized with an oxidizing agent, preferably at room temperature to 300° C. to obtain the spherical porous infusible pitch having a non-fusibility to heat. As the oxidizing agent, for example, oxygen gas ($O_2$), or a gas mixture prepared by diluting oxygen gas ($O_2$) with air, nitrogen or the like may be used.

The metal-containing spherical carbonaceous material can be prepared by, for example, (1) addition to the pitch, (2) impregnation to the porous pitch, (3) impregnation to the porous infusible pitch, (4) impregnation to the spherical carbon prepared by heating the porous infusible pitch, or (5) impregnation to the spherical activated carbon prepared by carrying out the treatment to impart infusibility. The addition or the impregnation of a metallic compound can be carried out by dissolving the metallic compound in a solvent, to prepare a metallic compound solution, adding or impregnating the solution to a carbon precursor, and heating to evaporate and remove the solvent, to thereby obtain a metal-containing pitch, a metal-containing spherical porous pitch, a metal-containing spherical porous infusible pitch, or a metal-containing spherical activated carbon, or the like. In case that the metallic compound is added to the pitch or impregnated to the spherical porous pitch, the above spherical activated carbon can be obtained by preparing the metal-containing spherical porous infusible pitch according to the above method; activating at 800° C. to 1000° C. in a gas stream having a reactivity to carbon, such as steam or carbon dioxide gas, or a gas mixture containing the above gas as a main component, to obtain a metal-containing porous spherical activated carbon, and washing with an acid to remove the metal. Further, in case that the metallic compound is impregnated to the spherical activated carbon, the above spherical activated carbon can be obtained by impregnating the metallic compound to the spherical activated carbon, carrying out the treatment to again impart infusibility, and washing with an acid to remove the metal.

Any metal which exhibits a catalytic effect in the steam activation can be used as the metal for preparing the metal-containing spherical carbonaceous material. The preferable metal is, for example, a transition metal, such as cobalt, iron, or nickel, a rare earth metal, such as yttrium, or a compound thereof, or a salt of the compound. The metallic compound or the salt of the compound may be, for example, an inorganic compound, such as a hydroxide, chloride, nitrate, or sulfate, an organic salt, such as acetylacetone salt or acetate, or an organic-inorganic complex salt, each containing the metallic element. The metal is introduced into carbon so that a metal atom concentration in the carbonaceous material before carrying out the activation treatment ranges preferably known 0.001 to 10% by weight, more preferably from 0.001 to 5% by weight.

The washing treatment is carried out to ensure a sufficient purity of the surface-modified spherical activated carbon from a standpoint of a safe oral administration. It is necessary to remove a metal content by washing with water, or an acidic solution of hydrochloric acid, nitric acid, sulfuric acid, or hydrofluoric acid. After washing, the metal content of the spherical activated carbon is preferably 150 ppm or less, more preferably 100 ppm or less, particularly preferably 50 ppm or less.

The resulting spherical activated carbon having large pores is oxidized at 300° C. to 800° C., preferably 320° C. to 600° C., in an atmosphere containing 0.1 to 50% by volume, preferably 1 to 30% by volume, particularly preferably 3 to 20% by volume of oxygen, and then reduced at 800° C. to 1200° C., preferably 800° C. to 1000° C., in an atmosphere of non-oxidative gas, to thereby obtain the surface-modified spherical activated carbon used as the adsorbent for oral administration according to the present invention. In the particular atmosphere containing oxygen, it is possible to use pure oxygen, nitrogen oxide, or air as an oxygen source. The atmosphere inactive to carbon means nitrogen, argon, or helium alone, or a combination thereof. The term "surface-modified spherical activated carbon" as used herein means a porous product prepared by the oxidizing and reducing treatments of the spherical activated carbon as above, wherein acidic and basic sites are added in a well-balanced manner on the surface of the spherical activated carbon, to thereby improve an adsorbability of harmful substances in an upper portion of a small intestine. For example, the specificity to toxins to be adsorbed can be improved by oxidizing and reducing the above spherical activated carbon.

It is important for the heat-infusible resin used as the starting material that a spherical product can be formed, and it is not fused or softened, and the shape is not changed, by a heat-treatment at a temperature of 500° C. or less. A heat-fusible resin can be preferably used, after being treated to impart infusibility, for example, oxidized, to thereby be converted to a state which can avoid a fusion oxidation.

A resin capable of obtaining a high carbonization yield by a heat-treatment is preferable as the heat-infusible resin used a starting material. If the carbonization yield is low, a strength of the spherical activated carbon becomes low. Further, undesirable pores are formed and a bulk density of the spherical activated carbon is lowered, and thus, a specific surface area per volume is lowered. Therefore, a volume to be orally administered is increased, and thus, a problem arises in that an oral administration becomes difficult. Accordingly, a heat-infusible resin having a higher carbonization yield is preferable. A yield by a heat-treatment at 800° C. in an atmosphere of non-oxidative gas is preferably 30% by weight or more, more preferably 35% by weight or more.

An ion-exchange resin is preferable as a heat-infusible resin used as a starting material, because an oral adsorbent having a high adsorbability of toxins to be removed can be produced. Generally, an ion-exchange resin comprises a copolymer (that is, a heat-fusible resin, such as a cross-linked vinyl resin) of divinylbenzene and styrene, acrylonitrile, acrylic acid, or methacrylic acid, and essentially has a structure wherein ion-exchange groups are bonded to a copolymer matrix having a three-dimensional network skeleton. The ion-exchange resin is generally classified, with respect to the kinds of ion-exchange groups, into a strongly acidic ion-exchange resin having sulfonic acid groups, a weakly acidic ion-exchange resin having carboxylic or sulfonic acid groups, a strongly basic ion-exchange resin having quaternary ammonium salts, and a weakly basic ion-exchange resin having primary or tertiary amines. In addition, a so-called hybrid ion-exchange resin having both acidic and basic ion-exchange groups is included as a special ion-exchange resin. In the present invention, all of the above ion-exchange resins may be used as a starting material.

The surface-modified spherical activated carbon wherein a volume of pores having a pore diameter of 7.5 to 15000 nm is from 0.25 mL/g to 1.0 mL/g can be obtained by carrying out the treatment to impart infusibility to the heat-infusible resin, particularly an ion-exchange resin, used as a carbon source according to the above-mentioned procedure.

A pitch may be used as a starting material. The pitch used as the starting material preferably has a high carbonization yield obtained by a heat treatment. If the carbonization yield is low, a strength of the spherical activated carbon becomes low. Further, undesirable pores are formed and a bulk density of the spherical activated carbon is lowered, and thus, a specific surface area per volume is lowered. Therefore, a volume to be orally administered is increased, and thus, a problem arises in that an oral administration becomes difficult. Accordingly, a pitch having a higher carbonization yield is preferable. A yield obtained by a heat-treatment at 800° C. in an atmosphere of non-oxidative gas is preferably 50% by weight or more, more preferably 60% by weight or more.

A cross-linked vinyl resin belonging to the heat-fusible resin is softened and melted when heated in an atmosphere of non-oxidative gas, and thus, only a carbonization yield of about 10% is obtained at best. However, when the cross-linked vinyl resin is oxidized at 150° C. to 400° C. in an atmosphere containing oxygen as a treatment to impart infusibility, a spherical carbonaceous material with a high carbonization yield of 30% or more can be obtained without softening or melting. A spherical activated carbon can be obtained by carrying out an activation treatment the same as that of the heat-infusible resin.

The cross-linked vinyl resin used as a starting material may be, for example, a porous spherical polymer prepared by an emulsion polymerization, a bulk polymerization, or a solution polymerization, preferably a porous spherical polymer prepared by a suspension polymerization.

For example, when the porous cross-linked vinyl resin is prepared by a suspension polymerization, an organic phase containing vinyl monomers, a cross-linking agent, porogen, and a polymerization initiator is added to an aqueous dispersion medium containing a dispersing agent, the whole is mixed with stirring to form many organic droplets suspended in an aqueous phase, and the monomers in the organic droplets are polymerized by heating, to thereby prepare the porous spherical cross-linked vinyl resin.

As the vinyl-based monomer, any vinyl-based monomer from which a spherical shape can be formed may be used. For example, an aromatic vinyl-based monomer, such as styrene, a styrene derivative wherein a hydrogen atom of a vinyl group or a phenyl group is substituted, or a compound wherein a heterocyclic or polycyclic compound is bonded instead of a phenyl group can be used. An example of the aromatic vinyl-based monomer may be α- or β-methyl styrene, α- or β-ethyl styrene, methoxy styrene, phenyl styrene, or chloro styrene, or, o-, m-, or p-methyl styrene, methoxy styrene, methylsilyl styrene, hydroxylstyrene, chlorostyrene, cyanostyrene, nitrostyrene, aminostyrene, carboxystyrene, or sulfoxystyrene, sodium styrene sulfonate, or vinyl pyridine, vinyl thiophene, vinyl pyrrolidone, vinyl naphthalene, vinyl anthracene, or vinylbiphenyl. Further, an aliphatic vinyl-based monomer can be used. For example, there may be mentioned vinyl esters such as ethylene, propylene, isobutylene, diisobutylene, vinyl chloride, acrylic acid ester, methacrylic acid ester, or vinyl acetate; vinylketones such as vinyl methyl ketone, or vinyl ethyl ketone; vinylaldehydes, such as acrolein, or methacrolein; or vinylethers, such as vinylmethylether, or vinylethylether.

Any cross-linking agent which may be used for the cross-lining of the above vinyl-based monomer may be used. For example, there may be mentioned divinylbenzene, divinylpyridine, divinyltoluene, divinylnaphthalene, diallyl phthalate, ethylene glycol diacrylate, ethylene glycol dimethylate, divinylxylene, divinylethylbenzene, divinylsulfone, polyvinyl or polyallyl ether of glycol or glycerol, polyvinyl or polyallyl ether of pentaerythritol, polyvinyl or polyallyl ether of mono or dithio derivative of glycol, polyvinyl or polyallyl ether of resorcinol, divinyl ketone, divinyl sulfide, allyl acrylate, diallyl maleate, diallyl fumarate, diallyl succinate, diallyl carbonate, diallyl malonate, diallyl oxalate, diallyl adipate, diallyl sebacate, triallyl tricarballylate, triallyl aconitate, triallyl citrate, triallyl phosphate, N,N'-methylene diacrylamide, 1,2-di (α-methylmethylene-sulfoneamido)ethylene, trivinylbenzene, trivinylnaphthalene, polyvinylanthracene, or trivinylcyclohexane. Particularly preferable cross-linking agent is polyvinyl aromatic hydrocarbon, such as divinylbenzene, glycol trimethacrylate such as ethylene glycol dimethacrylate, or polyvinyl hydrocarbon such as trivinyl cyclohexane). Divinylbenzene is most preferable, because of an excellent property of thermal decomposition.

As an appropriate porogen, there may be mentioned alkanoyl having 4 to 10 carbon atoms, such as, n-butanol, sec-butanol, 2-ethylhexanol, decanol, or 4-methyl 2-pentanol, alkyl ester having at least 7 carbon atoms, such as n-hexyl acetate, 2-ethylhexyl acetate, methyl oleate, dibutyl cebacate, dibutyl adipate, or dibutylcarbonate, alkyl ketone having 4 to 10 carbon atoms, such as dibutyl ketone or methyl isobutyl ketone, or alkyl carboxylic acid, such as heptanoic acid, aromatic hydrocarbon, such as toluene, xylene, or benzene, higher saturated aliphatic hydrocarbon, such as hexane, heptane, or isooctane, or cyclic aliphatic hydrocarbon, such as cyclohexane.

A polymerization initiator is not particularly limited, and an initiator usually used in this field can be used in the present invention. An initiator which is soluble in a polymerizable monomer and oil soluble is preferable. As an example of the polymerization initiator, there may be mentioned a dialkyl peroxide, a diacyl peroxide, a peroxyester, a peroxydicarbonate, or an azo compound. More particularly, a dialkyl peroxide, such as methylethylperoxide, di t-butyl peroxide, or dicumyl peroxide; a diacyl peroxide, such as isobutylperoxide, benzoylperoxide, 2,4-dichloro-benzoylperoxide, or 3,5, 5-trimethylhexanoyl peroxide; a peroxyester, such as t-butylperoxypyvalate, t-hexyl-peroxypyvalate, t-butylperoxyneodecanoate, t-hexylperoxy-neodecanoate, 1-cyclohexyl 1-methylethylperoxy-neodecanoate, 1,1,3,3-tetramethylbutylperoxyneodecanoate, cumyl peroxy-neodecanoate, or (α,α-bisneodecanoyl peroxy)diisopropyl-benzene; a peroxydicarbonate, such as bis(4-t-butyl-cyclohexyl) peroxy-dicarbonate, di n-propyl-oxy dicarbonate, diisopropyl peroxydicarbonate, di(2-ethylethylperoxy)-dicarbonate, dimethoxybutylperoxydicarbonate, di(3-methyl 3-methoxybutylperoxy)dicarbonate; or an azo compound, such as 2,2'-azobisisobutylonitorile, 2,2'-azobis(4-methoxy2,4-dimethylvaleronitrile, 2,2'-azobis(2,4-dimethylvaleronitrile), or 1,1'-azobis(1-cyclohexanecarbonitrile).

The surface-modified spherical activated carbon used as the adsorbent for oral administration of the present invention has an average diameter of 0.01 to 1 mm. If the average diameter of the surface-modified spherical activated carbon is less than 0.01 mm, an exterior surface area of the surface-modified spherical activated carbon is increased, and useful substances such as digestive enzymes are easily adsorbed. That is unfavorable. When the average diameter is more than 1 mm, a diffusion distance of toxic substances to the inside of the surface-modified spherical activated carbon is increased, and an adsorption rate is lowered. That, too, is unfavorable. The average diameter is preferably 0.02 to 0.8 mm.

In the surface-modified spherical activated carbon used as the adsorbent for oral administration of the present invention, a specific surface area (referred to as "SSA" hereinafter) determined by a BET method is 700 $m^2$/g or more. When the surface-modified spherical activated carbon has an SSA of less than 700 $m^2$/g, an adsorbability of toxic substances is unfavorably lowered. The SSA is preferably 1000 $m^2$/g or more. The upper limit of the SSA is not particularly limited, but the SSA is preferably 3000 $m^2$/g or less in view of a bulk density and strength.

In the surface-modified spherical activated carbon used as the adsorbent for oral administration of the present invention, a volume of pores having a pore diameter of 7.5 to 15000 nm is from 0.25 mL/g to 1.0 mL/g, preferably 0.3 mL/g to 0.8 mL/g. When the volume of pores having a pore diameter of 7.5 to 15000 nm is less than 0.25 mL/g, the adsorbability of harmful substances may be lowered. When the volume of pores having a pore diameter of 7.5 to 15000 nm is more than 1.0 mL/g, an adsorbed amount of useful substances, such as digestive enzymes, may be increased.

In a constitution of functional groups of the surface-modified spherical activated carbon used as the adsorbent for oral administration of the present invention, a total amount of acidic groups is 0.30 to 1.20 meq/g, and a total amount of basic groups is 0.20 to 0.7 meq/g. When the constitution of functional groups does not satisfy the condition that a total amount of acidic groups is 0.30 to 1.20 meq/g, and a total amount of basic groups is 0.20 to 0.7 meq/g, an adsorbability of harmful substances is unfavorably lowered. The total amount of acidic groups is preferably 0.30 meq/g to 1.00 meq/g, and the total amount of basic groups is preferably 0.30 meq/g to 0.60 meq/g.

Properties of the surface-modified spherical activated carbon used as the adsorbent for oral administration of the present invention, namely, the average particle diameter, the specific surface area, the pore volume, the total amount of acidic groups, and the total amount of basic groups, are measured by the following methods.

(1) An Average Particle Diameter

A particle-sizes accumulating standard curve with respect to a volume basis is prepared by a laser diffraction apparatus for measuring particle size distribution [SALAD-3000S; Shimadze Corporation]. A particle size at a particle-sizes accumulating ratio of 50% is determined as an average particle diameter.

(2) A Specific Surface Area (Method for Calculating a Specific Surface Area by a BET Method)

An amount of gas adsorbed is measured by a specific surface area measuring apparatus (for example, Flow Sorb II 2300 manufactured by MICROMERITICS) in accordance with a gas adsorbing method of a continuous flow for the surface-modified spherical activated carbon sample, and a specific surface area can be calculated by a BET equation. More particularly, the surface-modified spherical activated carbon is charged as a sample in a sample tube. A helium gas stream containing 30% by volume of nitrogen is passed through the sample tube, and an amount of nitrogen adsorbed to the surface-modified spherical activated carbon sample is measured by the following procedures. Specifically, the sample tube is cooled to $-196°$ C., whereby nitrogen is adsorbed to the surface-modified spherical activated carbon sample, and then the temperature of the sample tube is raised to room temperature. During the raising of the temperature, nitrogen is emitted from the surface-modified spherical activated carbon sample. The amount of nitrogen emitted is measured by a heat conductivity type detector as an amount (v) of gas adsorbed.

A value $v_m$ is calculated in accordance with a one-point method (relative pressure x=0.3) by a nitrogen adsorption at a temperature of liquid nitrogen, using an approximate equation:

$$v_m = 1/(v \cdot (1-x))$$

derived from the BET equation. Then, a specific surface area of the sample is calculated by an equation:

$$\text{specific surface area} = 4.35 \times v_m (m^2/g).$$

In the above equations, v is an adsorption amount $(cm^3/g)$ actually found, and x is a relative pressure.

(3) A Pore Volume by a Mercury Injection Method

The pore volume can be measured by a mercury porosimeter (for example, AUTOPORE 9200 manufactured by MICROMERITICS). The surface-modified spherical activated carbon is charged as a sample in a sample vessel, and degassed under a pressure of 2.67 Pa or less for 30 minutes. Then, mercury is introduced into the sample vessel, a pressure applied is gradually increased (maximum pressure=414 MPa) to force the mercury into the micropores in the surface-modified spherical activated carbon sample. A pore volume distribution of the surface-modified spherical activated carbon sample is measured from a relationship between the pressure and an amount of forced mercury, by equations as mentioned below. Specifically, a volume of mercury inserted into the surface-modified spherical activated carbon sample while a pressure is applied is increased from a pressure (0.06 MPa) corresponding to a pore diameter of 15 μm to the maximum pressure (414 MPa) corresponding to a pore diameter of 3 nm. A pore diameter can be calculated as follows. When mercury is forced into a cylindrical micropore having a diameter (D) by applying a pressure (P), a surface tension (γ) of mercury is balanced with a pressure acting on a section of the micropore, and thus, a following equation is held:

$$-\pi D \gamma \cos\theta = \pi (D/2)^2 \cdot P$$

wherein θ is a contact angle of mercury and a wall of the micropore. Therefore, a following equation:

$$D = (-4\gamma \cos\theta)/P$$

is held.

In the present specification, the relationship between the pressure (P) and the pore diameter (D) is calculated by an equation:

$$D = 1.27/P$$

given that a surface tension of mercury is 484 dyne/cm, a contact angle of mercury and carbon is 130°, a unit of the pressure P is MPa, and a unit of the pore diameter D is μm. The volume of pores having a pore diameter of 7.5 to 15000 nm in the present invention corresponds to a volume of mercury inserted by applying a pressure increasing from 0.085 MPa to 169 MPa.

(4) Total Amount of Acidic Groups

The total amount of acidic groups is an amount of NaOH consumed, which may be determined by adding 1 g of the surface-modified spherical activated carbon sample, after being crushed to form particles having a size of 200 mesh or less, to 50 mL of a 0.05N NaOH solution, shaking the mixture for 48 hours, then filtering out the surface-modified spherical activated carbon sample, and titrating until neutralization.

(5) Total Amount of Basic Groups

The total amount of basic groups is an amount of HCl consumed, which may be determined by adding 1 g of the surface-modified spherical activated carbon sample after being crushed to form particles having a size 200 mesh or less, to 50 mL of a 0.05N HCl solution, shaking the mixture for 24 hours, then filtering out the surface-modified spherical activated carbon sample, and titrating until neutralization.

As shown in Examples mentioned below, the surface-modified spherical activated carbon used as the adsorbent for oral administration of the present invention exhibits an excellent adsorbability of exacerbation factors of liver diseases or harmful substances of renal diseases, and therefore, may be used as an adsorbent for oral administration for treating or preventing a renal disease or a liver disease.

As the renal disease, there may be mentioned, for example, chronic renal failure, acute renal failure, chronic pyelonephritis, acute pyelonephritis, chronic nephritis, acute nephritic syndrome, acute progressive nephritic syndrome, chronic nephritic syndromes nephrotic syndrome, nephrosclerosis, interstitial nephritis, tubulopathy, lipoid nephrosis, diabetic nephropathy, renovascular hypertension, or hypertension syndrome, or secondary renal diseases caused by these primary diseases, or a light renal failure before a dialysis therapy, and may be used in an improvement of a light renal failure before a dialysis therapy or a disease condition for a patient during a dialysis therapy (see "Clinical Nephrology", Asakura-shoten, Nishio Honda, Kenkichi Koiso, and Kiyoshi Kurokawa, 1990; and "Nephrology" Igaku-shoin, Teruo Omae and Sei Fujimi, ed., 1981).

As the liver disease, there may be mentioned, for example, fulminant hepatitis, chronic hepatitis, viral hepatitis, alcoholic hepatitis, hepatic fibrosis, liver cirrhosis, hepatic cancer, autoimmune hepatitis, drug allergic hepatopathy, primary biliary cirrhosis, tremor, encephalopathia, dysbolism, or dysfunction. Further, the porous spherical carbonaceous substance can be used in a treatment of a disease caused by toxic substances in a body, such as psychosis.

Therefore, when the adsorbent for oral administration is used as an agent for treating or preventing a renal disease, it contains the surface-modified spherical activated carbon as an effective component. When the adsorbent for oral administration according to the present invention is used as an agent for a treatment of a liver or renal disease, a dosage thereof depends on the subject (human or other animal), age, individual differences, disease conditions, and so on. Therefore, in some cases, a dosage outside of the following dosage may be appropriate, but in general, the oral dosage in the case of a human is usually 1 to 20 g of the adsorbent per day, wherein the daily dosage may be divided into three to four portions. The dosage may be appropriately varied with the disease conditions. The formulation may be administered in any form, such as powders, granules, tablets, sugar-coated tablets, capsules, suspensions, sticks, divided packages, or emulsions. In the case of capsules, the usual gelatin capsules, or if necessary, enteric capsules may be used. In the case of tablets, the formulations must be broken into the original fine particles inside the body. The adsorbent may be used as a mixture with an electrolyte-controlling agent, such as an aluminum gel or Kayexalate.

The surface-modified spherical activated carbon of the present invention wherein a volume of pores having a pore diameter of 7.5 to 15000 nm is from 0.25 mL/g to 1.0 mL/g can be used as an agent for treating or preventing a renal or liver disease, in the form of a mixture with a conventionally known spherical activated carbon, that is, a spherical activated carbon or a surface-modified spherical activated carbon wherein a volume of pores having a pore diameter of 7.5 to 15000 nm is outside the above scope. Further, the surface-modified spherical activated carbon of the present invention wherein a volume of pores having a pore diameter of 7.5 to 15000 nm is from 0.25 mL/g to 1.0 mL/g can be used as an agent for treating or preventing a renal or liver disease, in combination with a conventionally known spherical activated carbon, that is, a spherical activated carbon or a surface-modified spherical activated carbon wherein a volume of pores having a pore diameter of 7.5 to 15000 nm is outside the above scope.

EXAMPLES

The present invention will now be further illustrated by, but is by no means limited to, the following Examples.

Example 1

An ion-exchange resin (styrene based; effective diameter=0.50 to 0.65 mm; trade name=Amberlite 15WET; Organo Corporation) which had been dried at 120° C. for 3 hours was sieved through a screen having an opening size of 250 μm, to remove fine powders. Then, the resulting spherical ion-exchange resin without fine powders was heated at 600° C. for 3 hours under a nitrogen gas atmosphere in a fluidized bed to obtain a spherical carbonaceous material. Then, 100 g of the resulting spherical carbonaceous material was charged into a vertical reaction quartz tube having a grating, and heated to 820° C. over 2 hours under a nitrogen gas atmosphere in a fluidized bed. Thereafter, the product was activated at 820° C. for 10 hours under an atmosphere of a nitrogen gas containing 64.5% by volume of steam to obtain 32 g of a spherical activated carbon.

The resulting spherical activated carbon was oxidized at 470° C. for 195 minutes under an atmosphere of a mixture of a nitrogen gas and 18.5% by volume of an oxygen gas in a fluidized bed, and then, reduced at 900° C. for 17 minutes under an atmosphere of a nitrogen gas in a fluidized bed to obtain a surface-modified spherical activated carbon. An average particle size was 0.35 mm.

The properties of the resulting surface-modified spherical activated carbon are listed in Tables 1 and 2.

Example 2

The procedure described in Example 1 was repeated, except that the activating time was 14 hours in the activating step to obtain 17 g of a surface-modified spherical activated carbon. An average particle size was 0.35 mm.

The properties of the resulting surface-modified spherical activated carbon are listed in Tables 1 and 2.

Example 3

Petroleum pitch (68 kg) (softening point=210° C., quinoline insoluble contents=not more than 1% by weight, ratio of hydrogen atoms/carbon atoms=0.63) and naphthalene (32 kg) were charged into an autoclave (internal volume=300 L) equipped with stirring fans, melted at 180° C., and mixed. Then, 68 g of acetylacetone cobalt salt was added to the pitch and dissolved by stirring. Thereafter, the mixture was cooled to 140° C. to 160° C. and extruded to form string-like shaped products. Then, the string-like shaped products were broken so that a ratio of a diameter to a length became about 1 to 2.

The resulting broken products were added to an aqueous solution prepared by dissolving 0.23% by weight of polyvinyl alcohol (saponification value=88%) and heating to 93° C., and dispersed with stirring to be spheroidized. Then, the whole was cooled by replacing the polyvinyl alcohol aqueous solution with water, at 20° C. for 3 hours, whereby the pitch was solidified and naphthalene crystals were precipitated, and a slurry of spherical shaped products of pitch was obtained.

After most of the water was removed by filtration, the naphthalene in the spherical shaped products of pitch was extracted and removed with n-hexane at an amount by weight of about 6 times that of the spherical shaped products of pitch. The resulting porous spherical pitch was heated to 235° C. by passing a heated air in a fluidized bed, and allowed to stand at 235° C. for 1 hour, to thereby be oxidized, and a porous spherical oxidized pitch was obtained, which was non-fusible to heat.

Thereafter, the resulting porous spherical oxidized pitch was activated in a fluidized bed at 820° C. for 1 hour by a nitrogen gas atmosphere containing 64.5% by volume of steam to obtain a spherical activated carbon. The resulting metal-containing spherical activated carbon was washed with 10% hydrochloric acid, filtrated, washed with ion-exchanged water until a pH of the filtrate reached 7, and dried in a nitrogen gas atmosphere. Further, the resulting spherical activated carbon was oxidized in the fluidized bed at 470° C. for 195 minutes under a nitrogen-oxygen atmosphere containing 18.5% by volume of oxygen, and reduced in the fluidized bed at 900° C. for 17 minutes under a nitrogen gas atmosphere, to obtain a surface-modified spherical activated carbon. An average particle size was 0.35 mm.

The properties of the resulting surface-modified spherical activated carbon are listed in Tables 1 and 2.

Example 4

The procedure described in Example 3 was repeated, except that the amount of acetylacetone cobalt salt used to the melted pitch was 6.8 g, and the activating time in the activating step was 2 hours, to obtain a surface-modified spherical activated carbon. An average particle size was 0.35 mm.

The properties of the resulting surface-modified spherical activated carbon are listed in Tables 1 and 2.

Example 5

Petroleum pitch (68 kg) (softening point=210° C.; quinoline insoluble contents=not more than 1% by weight; ratio of hydrogen atoms/carbon atoms=0.63) and naphthalene (32 kg) were charged into an autoclave (internal volume=300 L) equipped with stirring fans, melted at 180° C., and mixed. Thereafter, the mixture was cooled to 140° C. to 160° C. and extruded to form string-like shaped products. Then, the string-like shaped products were broken so that a ratio of a diameter to a length became about 1 to 2.

The resulting broken products were added to an aqueous solution prepared by dissolving 0.23% by weight of polyvinyl alcohol (saponification value=88%) and heating to 93° C., and dispersed with stirring to be spheroidized. Then, the whole was cooled by replacing the polyvinyl alcohol aqueous solution with water, at 20° C. for 3 hours, whereby the pitch was solidified and naphthalene crystals were precipitated, and a slurry of spherical shaped products of pitch was obtained.

After most of the water was removed by filtration, the naphthalene in the spherical shaped products of pitch was extracted and removed with n-hexane at an amount by weight of about 6 times that of the spherical shaped products of pitch. The resulting porous spherical pitch was heated to 235° C. by passing a heated air in a fluidized bed, and allowed to stand at 235° C. for 1 hour, to thereby be oxidized, and a porous spherical oxidized pitch was obtained, which was non-fusible to heat.

Thereafter, the resulting porous spherical oxidized pitch was activated in a fluidized bed at 820° C. for 230 minutes by a nitrogen gas atmosphere containing 64.5% by volume of steam to obtain a porous spherical carbon having a packing density of 0.6 mL/g.

Then, 50 g of the resulting porous spherical carbon was impregnated with a solution prepared by dissolving 0.3 g of acetylacetone cobalt salt in 5 of toluene, and toluene was evaporated under a reduced pressure. The resulting cobalt salt-impregnated activated carbon was activated in a fluidized bed at 820° C. for 8 minutes by a nitrogen gas atmosphere containing 64.5% by volume of steam. The resulting metal-containing spherical activated carbon was washed with 10% hydrochloric acid, filtrated, washed with ion-exchanged water until the pH of the filtrate reached 7, and dried in a nitrogen gas atmosphere.

Further, the resulting spherical activated carbon was oxidized in the fluidized bed at 470° C. for 195 minutes under a nitrogen-oxygen atmosphere containing 18.5% by volume of oxygen, and reduced in the fluidized bed at 900° C. for 17 minutes under a nitrogen gas atmosphere, to obtain a surface-modified spherical activated carbon. An average particle size was 0.35 mm.

The properties of the resulting surface-modified spherical activated carbon are listed in Tables 1 and 2.

Example 6

Ion-exchanged water (658 g) and 1.44% methyl cellulose aqueous solution (32 g) were charged into a 1 L separable flask. Further, 109 g of styrene, 120 g of divinyl benzene with a purity of 57% (57% divinylbenzene and 43% ethylvinyl benzene), 1.3 g of 2,2'-azobis(2,4-dimethylvaleronitrile), and an appropriate amount of 1-butanol as a porogen were added thereto. Then, a replacement with a nitrogen gas was carried out. The two-phase system was stirred at 150 rpm, and heated to 55° C., and then allowed to stand for 20 hours. The resulting resin was filtered, and dried under a reduced pressure at 90° C. for 12 hours in a vacuum dryer to thereby evaporate water and porogen under a reduced pressure. A spherical porous synthetic resin having an average particle size of 600 μm was obtained. A specific surface area of the porous synthetic resin was 30 m²/g.

The resulting spherical porous synthetic resin (100 g) was charged into a reactor having a grating, and treated to impart infusibility in a vertical tubular furnace. The infusibility-imparting treatment was carried out under the conditions that dried air (3 L/min) was upwardly passed from the lower portion of the reactor tube, the temperature was raised to 260° C. at a rate of 5° C./h, and the whole was allowed to stand at 260° C. for 4 hours. The resulting spherical porous oxidized resin was heat-treated at 600° C. for 1 hour under a nitrogen atmosphere, and then activated in a fluidized bed at 820° C. for 10 hours under a nitrogen gas atmosphere containing 64.5% by volume of steam, to obtain a spherical activated carbon The resulting spherical activated carbon was oxidized in the fluidized bed at 470° C. for 195 minutes under a nitrogen-oxygen atmosphere containing 18.5% by volume of oxygen, and reduced in the fluidized bed at 900° C. for 17 minutes under a nitrogen gas atmosphere, to obtain a surface-modified spherical activated carbon. An average particle size was 310 μm.

The properties of the resulting surface-modified spherical activated carbon are listed in Tables 1 and 2.

Comparative Example 1

Petroleum pitch (68 kg) (softening point=178° C.; quinoline insoluble contents=not more than 1% by weight; ratio of hydrogen atoms/carbon atoms=0.67) and naphthalene (32 kg) were charged into an autoclave (internal volume=300 L) equipped with stirring fans, melted at 200° C., and mixed. The mixture was cooled to 140° C. to 160° C. and extruded to form string-like shaped products. Then, the string-like shaped products were broken so that a ratio of a diameter to a length became about 1 to 2.

The resulting broken products were added to an aqueous solution prepared by dissolving 0.23% by weight of polyvinyl alcohol (saponification value=88%) and heating to 93° C., and dispersed with stirring to be spheroidized. Then, the whole was cooled by replacing the polyvinyl alcohol aqueous solution with water, at 20° C. for 3 hours, whereby the pitch was solidified and naphthalene crystals were precipitated, and a slurry of spherical shaped products of pitch was obtained.

After most of the water was removed by filtration, the naphthalene in the spherical shaped products of pitch was extracted and removed with n-hexane at an amount by weight of about 6 times that of the spherical shaped products of pitch. The resulting porous spherical pitch was heated to 235° C. by passing a heated air in a fluidized bed, and allowed to stand at 235° C. for 1 hour, to thereby be oxidized, and a porous spherical oxidized pitch was obtained, which was non-fusible to heat.

Thereafter, the resulting porous spherical oxidized pitch was activated in a fluidized bed at 820° C. for 400 minutes under a nitrogen gas atmosphere containing 64.5% by volume of steam to obtain a spherical activated carbon having a packing density of 0.5 mL/g. The resulting spherical activated carbon was oxidized in the fluidized bed at 470° C. for 195 minutes under a nitrogen-oxygen atmosphere containing 18.5% by volume of oxygen, and reduced in the fluidized bed at 900° C. for 17 minutes under a nitrogen gas atmosphere, to obtain a surface-modified spherical activated carbon. An average particle size was 0.35 mm.

The properties of the resulting surface-modified spherical activated carbon are listed in Tables 1 and 2.

Comparative Example 2

An ion-exchange resin (styrene based; effective diameter=0.50 to 0.65 mm; trade name=Amberlite 15WET; Organo Corporation) which had been dried at 120° C. for 3 hours was sieved through a screen having an opening size of 250 μm, to remove fine powders. Then, the resulting spherical ion-exchange resin without fine powders was heated at 600° C. for 3 hours under a nitrogen gas atmosphere in a fluidized bed to obtain a spherical carbonaceous material. Then, 100 g of the resulting spherical carbonaceous material was charged into a vertical reaction quartz tube having a grating, and heated to 820° C. over 2 hours under a nitrogen gas atmosphere in a fluidized bed. Thereafter, the product was activated at 820° C. for 10 hours under an atmosphere of a nitrogen gas containing 64.5% by volume of steam to obtain 32 g of a spherical activated carbon. An average particle size was 0.35 mm.

The properties of the resulting surface-modified spherical activated carbon are listed in Tables 1 and 2.

Comparative Example 3

Spherical phenolic resin (particle diameter=10 to 700 μm: trade name=High functional true spherical resin "Maririn" HF500 type; Gun Ei Chemical Industry Co., Ltd.) was sieved through a screen having an opening size of 250 μm, to remove fine powders. Then, 150 g of the resulting spherical phenolic resin without fine powders was charged into a vertical reaction quartz tube having a grating, and heated in a fluidized bed at 900° C. for 1 hour under a nitrogen gas atmosphere to obtain 68 g of a spherical carbonaceous material. Thereafter, 68 g of the resulting spherical carbonaceous material was charged into a vertical reaction quartz tube having a grating, heated in a fluidized bed to 900° C. over 2.5 hours, and activated at 900° C. under a nitrogen gas atmosphere containing 64.5% by volume of steam to obtain 30 g of a spherical activated carbon having a packing density of 0.5 mL/g.

The resulting spherical activated carbon was further oxidized in the fluidized bed at 470° C. for 195 minutes under a nitrogen-oxygen atmosphere containing 18.5% by volume of oxygen, and reduced in the fluidized bed at 900° C. for 17 minutes under a nitrogen gas atmosphere, to obtain a surface-modified spherical activated carbon. An average particle size was 0.28 mm.

The properties of the resulting surface-modified spherical activated carbon are listed in Tables 1 and 2.

Comparative Example 4

The procedure described in Comparative Example 3 was repeated, except that a spherical phenolic resin (particle diameter=700 μm: trade name=Spherical cured phenolic resin ACS series PR-ACS-2-50C; Sumitomo Bakelite Co., Ltd.) was used instead of the spherical phenolic resin used in Comparative Example 3, i.e., the spherical phenolic resin manufactured by Gunei Kagaku K. K., to obtain a surface-modified spherical activated carbon. An average particle size was 0.41 mm.

The properties of the resulting surface-modified spherical activated carbon are listed in Tables 1 and 2.

Method for Evaluation of the Oral Adsorbents

The properties shown in Tables 1 and 2 were measured by the following methods.

(1) Pore Volume

The surface-modified spherical activated carbon or the activated carbon prepared in Examples 1 to 5 and Comparative Examples 1 to 4 was measured by the mercury injection method as mentioned above. The values shown in Table 1 correspond to volumes of pores having a pore diameter of 7.5 to 15000 nm and a pore diameter of 20 to 15000 nm (2) Total Amount of Acidic and Basic Groups The surface-modified spherical activated carbon sample (1 g) which had been crushed to form particles having a size of 200 mesh or less was added to 50 mL of a 0.05N NaOH solution (total acidic groups) or 50 mL of a 0.05N HCl solution (total basic groups), and the mixture was shaken for 48 hours. The surface-modified spherical activated carbon sample was filtered out, and an amount of NaOH consumed (total acidic groups) or an amount of HCl consumed (total basic groups) was determined by a neutralization titration.

(3) Test for Measuring Residual Amount of DL-β-aminoisobutyric Acid

An adsorption test of DL-β-aminoisobutyric acid for the surface-modified spherical activated carbon or the activated carbon prepared in Examples 1 to 5 and Comparative Examples 1 to 4 was carried out as follows.

The spherical activated carbon sample or the surface-modified spherical activated carbon sample was dried, and 0.500 g of the dried sample was accurately weighed and charged into a conical flask equipped with a ground-in stopper. On the other hand, 0.100 g of DL-β-aminoisobutyric acid was accurately weighed and dissolved by adding a phosphate buffer (pH 7.4) to prepare a stock solution having an accurate volume of 1000 mL. The stock solution in an accurate amount of 50 mL was charged to the conical flask equipped with a ground-in stopper. The flask was shaken at 37±1° C. for 3 hours. The product in the flask was filtered with suction through a 0.65 μm membrane filter. A first filtrate (about 20 mL) was discarded, and a subsequent filtrate (about 10 mL) was taken as a sample solution.

Then, 0.1 mL of the sample solution was accurately weighed and charged in a test tube. A phosphate buffer (pH 8.0) was added in an accurate amount of 5 mL thereto, and the whole was mixed. Thereafter, a solution prepared by dissolving 0.100 g of fluorescamine in 100 mL of acetone (for a non-aqueous titration) was added in an accurate amount of 1 mL, and the whole was mixed and allowed to stand for 15 minutes. The resulting solution was analyzed by fluorometry, and the fluorescence was measured at an excitation wavelength of 390 nm and a fluorescent wavelength of 475 nm.

A standard curve was prepared by producing 100 mL of a mixture of 0 mL, 15 mL, 50 mL, 75 mL, and 100 mL of the DL-β-aminoisobutyric acid stock solution and the balance of a phosphate buffer (pH 7.4), stirring and filtering the mixture, charging the resulting filtrate in an accurate amount of 0.1 mL to a test tube, adding a phosphate buffer (pH 8.0) in an accurate amount of 5 mL, mixing the whole, adding a solution (an accurate amount: 1 mL) prepared by dissolving 0.100 g of fluorescamine in 100 mL of acetone (for a non-aqueous titration), mixing the whole, allowing to stand for 15 minutes, analyzing the resulting solution by fluorometry, and measuring the fluorescence at an excitation wavelength of 390 nm and a fluorescent wavelength of 475 nm. Finally, an amount (mg/dL) of remaining DL-β-aminoisobutyric acid in the solution was calculated, using the standard curve.

The values shown in Table 2 indicate evaluations from "10" (non-adsorbed) to "0" (completely adsorbed).

(4) Test for Measuring Changes of Residual Amount of DL-β-aminoisobutyric Acid

In the above-mentioned test (3), "Test for measuring residual amount of DL-β-aminoisobutyric acid", the spherical activated carbon sample or the surface-modified spherical activated carbon sample was brought into contact with and shaken with DL-β-aminoisobutyric acid for a predetermined period of time, i.e., for 3 hours. On the contrary, in the present test (4), the shaking time was varied and a change of an adsorption rate was measured for the surface-modified spherical activated carbon prepared by Comparative Example 1.

The residual amounts of DL-β-aminoisobutyric acid were determined according to the method mentioned in the above item (3) when an initial concentration of DL-β-aminoisobutyric acid was 10 mg/dL, and the shaking time was 1 hour, 2 hours, 3 hours, 5 hours, 8 hours, 18 hours or 24 hours. The results are shown in FIG. 1 wherein the data for the surface-modified spherical activated carbon prepared in Example 5 (shaking time=3 hours) is also shown as a reference.

(5) Specific Surface Area

The specific surface area was measured by the above-mentioned BET method.

TABLE 1

| Examples | Starting material | Pore volume (mL/g) Pore diameter 7.5-15000 nm | Pore volume (mL/g) Pore diameter 20-15000 nm | Total acidic groups (meq/g) | Total basic groups (meq/g) |
|---|---|---|---|---|---|
| Example 1 | Ion-exchange resin | 0.42 | 0.25 | 0.65 | 0.59 |
| Example 2 | Ion-exchange resin | 0.45 | 0.27 | 0.65 | 0.58 |
| Example 3 | Pitch | 0.64 | 0.54 | 0.58 | 0.55 |
| Example 4 | Pitch | 0.40 | 0.21 | 0.56 | 0.57 |
| Example 5 | Pitch | 0.27 | 0.12 | 0.57 | 0.54 |
| Example 6 | Cross-linked vinyl resin | 0.41 | 0.22 | 0.57 | 0.56 |
| Comparative Example 1 | Pitch | 0.23 | 0.13 | 0.56 | 0.55 |
| Comparative Example 2 | Ion-exchange resin | 0.41 | 0.27 | 0.17 | 0.60 |
| Comparative Example 3 | Phenol resin | 0.04 | 0.02 | 0.67 | 0.72 |
| Comparative Example 4 | Phenol resin | 0.06 | 0.03 | 0.56 | 0.57 |

TABLE 2

| Examples | Residual amount of β-aminoisobutyric acid (mg/dL) | Specific surface area (m²/g) | Average particle size (mm) |
|---|---|---|---|
| Example 1 | 3.9 | 1250 | 0.35 |
| Example 2 | 3.6 | 1350 | 0.35 |
| Example 3 | 3.9 | 1510 | 0.35 |
| Example 4 | 4.0 | 1490 | 0.35 |
| Example 5 | 4.5 | 1373 | 0.35 |
| Example 6 | 3.9 | 1500 | 0.31 |
| Comparative Example 1 | 6.5 | 1520 | 0.35 |
| Comparative Example 2 | 7.9 | 1330 | 0.35 |
| Comparative Example 3 | 4.8 | 1609 | 0.28 |
| Comparative Example 4 | 5.1 | 1515 | 0.41 |

The adsorbent for oral administration according to the present invention can be used as an adsorbent for oral administration for treating or preventing a renal disease, or an adsorbent for treating or preventing a liver disease.

As the renal disease, there may be mentioned, for example, chronic renal failure, acute renal failure, chronic pyelonephritis, acute pyelonephritis, chronic nephritis, acute nephritic syndrome, acute progressive nephritic syndrome, chronic nephritic syndromes nephrotic syndrome, nephrosclerosis, interstitial nephritis, tubulopathy, lipoid nephrosis, diabetic nephropathy, renovascular hypertension, or hypertension syndrome, or secondary renal diseases caused by these primary diseases, or a light renal failure before a dialysis therapy, and may be used in an improvement of a light renal failure before a dialysis therapy or a disease condition for a patient during dialysis therapy (see "Clinical Nephrology", Asakura-shoten, Nishio Honda, Kenkichi Koiso, and Kiyoshi Kurokawa, 1990; and "Nephrology" Igaku-shoin, Teruo Omae and Sei Fujimi, ed., 1981).

As the liver disease, there may be mentioned, for example, fulminant hepatitis, chronic hepatitis, viral hepatitis, alcoholic hepatitis, hepatic fibrosis, liver cirrhosis, hepatic cancer, autoimmune hepatitis, drug allergic hepatopathy, primary biliary cirrhosis, tremor, encephalopathia, dysbolism, or dysfunction. Further, the porous spherical carbonaceous substance can be used in a treatment of a disease caused by toxic substances in a body, such as psychosis.

As above, the present invention was explained with reference to particular embodiments, but modifications and improvements obvious to those skilled in the art are included in the scope of the present invention.

The invention claimed is:

1. An adsorbent for an oral administration, comprising a surface-modified spherical activated carbon wherein the average diameter is 0.01 to 1 mm, a specific surface area determined by a BET method is 700 m²/g or more, a volume of pores having a pore diameter of 7.5 to 15000 nm is from 0.25 mL/g to 1.0 mL/g, a volume of pores having a pore diameter of 7.5 to less than 20 nm is from 0.10 mL/g to 0.19 mL/g, a total amount of acidic groups is 0.30 to 1.20 meq/g, and a total amount of basic groups is 0.20 to 0.7 meq/g.

2. A pharmaceutical composition comprising a surface-modified spherical activated carbon wherein the average diameter is 0.01 to 1 mm, a specific surface area determined by a BET method is 700 m²/g or more, a volume of pores having a pore diameter of 7.5 to 15000 nm is from 0.25 mL/g to 1.0 mL/g, a volume of pores having a pore diameter of 7.5 to less than 20 nm is from 0.10 mL/g to 0.19 mL/g, a total amount of acidic groups is 0.30 to 1.20 meq/g, and a total amount of basic groups is 0.20 to 0.7 meq/g.

3. The adsorbent for oral administration according to claim 1, wherein a carbon source for the surface-modified spherical activated carbon is a heat fusible resin.

4. The adsorbent for oral administration according to claim 1, wherein a carbon source for the surface-modified spherical activated carbon is a heat-infusible resin.

5. The adsorbent for oral administration according to claim 1, wherein a carbon source for the surface-modified spherical activated carbon is a pitch.

6. The adsorbent for oral administration according to claim 1, wherein the surface-modified spherical activated carbon is prepared by oxidizing a spherical activated carbon at 300-800° C. and then reducing the product at 800-1200° C.

7. The adsorbent for oral administration according to claim 1, wherein the average diameter is 0.02 to 0.8 mm, a specific surface area determined by a BET method is from 1000-3000 $m^2/g$, a volume of pores having a pore diameter of 7.5 to 15000 nm is from 0.3 mL/g to 0.8 mL/g, a volume of pores having a pore diameter of 7.5 to less than 20 nm is from 0.10 mL/g to 0.19 mL/g, and a total amount of basic groups is 0.30 to 0.60 meq/g.

8. A method for treating a renal disease, comprising administering to a subject in need thereof, a surface-modified spherical activated carbon wherein an average diameter is 0.01 to 1 mm, a specific surface area determined by a BET method is 700 $m^2/g$ or more, a volume of pores having a pore diameter of 7.5 to 15000 nm is from 0.25 mL/g to 1.0 mL/g, a volume of pores having a pore diameter of 7.5 to less than 20 nm is from 0.10 mL/g to 0.19 mL/g, a total amount of acidic groups is 0.30 to 1.20 meq/g, and a total amount of basic groups is 0.20 to 0.7 meq/g.

9. The method according to claim 8, wherein the renal disease is a disease selected from the group consisting of chronic renal failure, acute renal failure, chronic pyelonephritis, acute pyelonephritis, chronic nephritis, acute nephritic syndrome, acute progressive nephritic syndrome, chronic nephritic syndrome, nephrotic syndrome, nephrosclerosis, interstitial nephritis, tubulopathy, lipoid nephrosis, diabetic nephropathy, renovascular hypertension, and hypertension syndrome, secondary renal diseases caused by these primary diseases, and a light renal failure before a dialysis therapy.

10. A method for treating a liver disease, comprising administering to a subject in need thereof, a surface-modified spherical activated carbon wherein an average diameter is 0.01 to 1 mm, a specific surface area determined by a BET method is 700 $m^2/g$ or more, a volume of pores having a pore diameter of 7.5 to 15000 nm is from 0.25 mL/g to 1.0 mL/g, a volume of pores having a pore diameter of 7.5 to less than 20 nm is from 0.10 mL/g to 0.19 mL/g, a total amount of acidic groups is 0.30 to 1.20 meq/g, and a total amount of basic groups is 0.20 to 0.7 meq/g.

11. The method according to claim 10, wherein the liver disease is a disease selected from the group consisting of fulminant hepatitis, chronic hepatitis, viral hepatitis, alcoholic hepatitis, hepatic fibrosis, liver cirrhosis, hepatic cancer, autoimmune hepatitis, drug allergic hepatopathy, primary biliary cirrhosis, tremor, encephalopathia, dysbolism, and dysfunction.

* * * * *